United States Patent [19]

Abrams et al.

[11] Patent Number: 4,737,592

[45] Date of Patent: Apr. 12, 1988

[54] SELECTED CHABAZITE ZEOLITES AS CATALYSTS FOR CONVERSION OF METHANOL AND AMMONIA TO DIEMETHYLAMINE

[75] Inventors: Lloyd Abrams, Hockessin, Del.; Robert D. Shannon, Chadds Ford, Pa.; George C. Sonnichsen, Wilmington, Del.

[73] Assignee: E. I. Du Pont de Nemours and Company, Wilmington, Del.

[21] Appl. No.: 909,238

[22] Filed: Sep. 19, 1986

Related U.S. Application Data

[63] Continuation-in-part of Ser. No. 672,490, Nov. 16, 1985, abandoned.

[51] Int. Cl.$^4$ .................. C07C 85/06; C07C 85/02
[52] U.S. Cl. ..................... 564/479; 564/474
[58] Field of Search ............... 672/490; 564/474, 479

[56] References Cited

U.S. PATENT DOCUMENTS

| | | | |
|---|---|---|---|
| Re. 19,632 | 7/1935 | Arnold | 260/127 |
| 1,926,691 | 9/1933 | Swallen et al. | 260/127 |
| 1,992,935 | 3/1935 | Arnold | 260/127 |
| 2,349,222 | 3/1944 | Goshorn | 260/585 |
| 2,394,515 | 2/1946 | Goshorn | 260/583 |
| 2,394,516 | 2/1946 | Goshorn | 260/583 |
| 2,456,599 | 12/1948 | Smith | 260/585 |
| 3,278,598 | 10/1966 | Markiewitz | 260/563 |
| 3,384,667 | 5/1968 | Hamilton | 260/585 |
| 3,387,032 | 6/1968 | Leonard | 260/585 |
| 4,082,805 | 4/1978 | Kaeding | 260/585 |
| 4,191,709 | 3/1980 | Parker et al. | 260/583 |
| 4,217,240 | 8/1980 | Bergma | 564/479 |
| 4,254,061 | 3/1981 | Weigert | 564/479 |
| 4,313,003 | 1/1982 | Weigert | 564/463 |
| 4,398,041 | 8/1983 | Cockran et al. | 564/479 |
| 4,434,300 | 2/1984 | Deeba et al. | 564/479 |
| 4,436,938 | 3/1984 | Tompsett | 564/474 |
| 4,602,112 | 7/1986 | Gier et al. | 564/474 |

FOREIGN PATENT DOCUMENTS

| | | |
|---|---|---|
| 0085408 | 2/1983 | European Pat. Off. |
| 57-169444 | 10/1982 | Japan . |
| 49340 | 3/1983 | Japan .................. 564/479 |
| 422563 | 1/1935 | United Kingdom . |

OTHER PUBLICATIONS

A. I. Ch. E. Jounal, 12:292, (1966), Restelli et al.
Journal of Catalysis 82:313, (1981), Mochida et al.

Primary Examiner—J. E. Evans

[57] ABSTRACT

A process is provided for producing dimethylamine, comprising reacting methanol and/or dimethylether and ammonia in amounts sufficient to provide a carbon/nitrogen (C/N) ratio from about 0.2 to about 1.5, at a temperature from about 250° C to about 450°C., in the presence of a catalytic amount of an acidic zeolite catalyst selected from the group consisting of natural, H-exchanged, and M-exchanged chabazites, each having a geometric selectivity index greater than about 3, wherein M is one or more alkali metal ions selected from the group consisting of Na, K, Rb, and Cs.

15 Claims, No Drawings

SELECTED CHABAZITE ZEOLITES AS CATALYSTS FOR CONVERSION OF METHANOL AND AMMONIA TO DIEMETHYLAMINE

CROSS-REFERENCE TO RELATED APPLICATION

This is a continuation-in-part of copending application bearing U.S. Ser. No. 672,490 filed Nov. 16, 1984, now abandoned.

BACKGROUND OF THE INVENTION

1. Field of the Invention

This invention involves a process for making amines, particularly dimethylamine, in which methanol and/or dimethylether and ammonia are contacted in the presence of a selected zeolite catalyst.

2. Background of the Invention

Methylamines are generally prepared in industrial quantities by continuous reaction of methanol and ammonia in the presence of a silica-alumina catalyst. The reactants are typically combined in the vapor phase, at temperatures in the range of 300° to 500° C., and at elevated pressures. Trimethylamine is the principal component of the resulting product stream, accompanied by lesser amounts of monomethylamine and dimethylamine. From a commercial standpoint, the most valued product of the reaction is dimethylamine, in view of its widespread industrial use as a chemical intermediate. Accordingly, a major objective of those seeking to enhance the commercial efficiency of this process has been to improve overall yields of dimethylamine, and to a lesser extent, monomethylamine, relative to trimethylamine. Among the approaches taken to meet this objective are recycling of trimethylamine, adjustment of the ratio of methanol to ammonia reactants, and use of selected dehydrating or aminating catalyst species. Due to the commercial importance of the process, a rather extensive compendium of patents and other contributions to the technical literature has resulted. Representative references generally relevant to the field of the present invention are summarized in the following paragraphs.

Swallen, U.S. Pat. No. 1,926,691, discloses a process for producing dimethylamine by disproportionating monomethylamine over dehydrating or aminating catalysts such as alumina, silica, thoria, aluminum silicate or partially dehydrated aluminum trihydrate.

Arnold, U.S. Pat. No. 1,922,935, describes a process for catalytic synthesis of amines from alcohols and ammonia which employs as catalyst a dehydrating oxide, e.g., alumina, deposited on the surface of a porous, rigid gel, e.g., silica gel. Arnold, U.S. Pat. No. Re. 19,632, discloses a process improvement in which trimethylamine is introduced with the methanol and ammonia reactants to shift reaction equilibrium in favor of dimethylamine production.

Johnson, British Pat. No. 422,563, discloses a process for producing aliphatic amines involving heating an alcohol or ether under a pressure of more than about 50 atmospheres in the presence of a "catalyst capable of splitting off water" (e.g., alumina), with an excess of ammonia and optionally with addition of primary amine to the reaction mixture.

Goshorn, U.S. Pat. No. 2,349,222, discloses use of granular alumina coated with one or more oxides of nickel, cobalt, or chromium as a catalyst for alkylation of ammonia to produce alkyl amines. Goshorn, U.S. Pat. Nos. 2,394,515 and 2,394,516, discloses use as catalyst of an aluminum salt or oxide coated with silica and vanadium or molybdenum oxide.

Smith, U.S. Pat. No. 2,456,599, discloses a process improvement wherein water is added to a reactant feed mixture of methanol and ammonia to repress formation of tertiary amine in favor of primary and secondary amine.

Markiewitz, U.S. Pat. No. 3,278,598, discloses use of a rhodium, palladium, or ruthenium cocatalyst in conjunction with Raney metals to increase production of secondary amines from the reaction of alcohols and ammonia.

Rostelli et al., *A. I. Ch. E. Journal* 12:292 (1966) describe studies of transmethylation reactions of monomethylamine and dimethylamine over montmorillonite, a hydrate magnesium or calcium oxide-containing aluminosilicate having a porous lattice structure. For transmethylation of monomethylamine, this work indicated that reaction rate was directly proportional to reactant partial pressure, indicating that the rate-determining event is adsorption of reactant to the catalyst surface.

Hamilton, U.S. Pat. No. 3,384,667, describes alkylation of ammonia in the presence of a dehydrated crystalline aluminosilicate catalyst having pores of a diameter permitting absorption of primary and secondary, but not tertiary, amine products. Among the many catalysts disclosed by this patent are the natural zeolites ferrierite, chabazite, erionite, and mordenite.

Leonard, U.S. Pat. No. 3,387,032, discloses a process for reacting ammonia with methanol and/or dimethyl ether in the presence of a catalyst consisting of a silica gel base impregnated with 10-15% alumina which is first steam-deactivated and then treated with silver, rhenium, molybdenum, or cobalt ions to promote selectivity for dimethylamine.

Kaeding, U.S. Pat. No. 4,082,805, discloses use of a crystalline aluminosilicate or zeolite catalyst having the structure of ZSM-5, ZSM-11 or ZSM-21 in a process for producing amines by reaction of ammonia with $C_1$-$C_5$ alcohols at elevated temperatures and pressures.

Parker et al., U.S. Pat. No. 4,191,709, describe use of a hydrogen form of zeolite FU-1 or zeolite FU-1 in which some or all of the protons have been replaced by bivalent or trivalent cations.

Weigert, U.S. Pat. No. 4,254,061, discloses a process in which production of monomethylamine is enhanced by reacting methanol and ammonia in amounts sufficient to provide a C/N ratio of 0.5 to 1.5 over a catalyst selected from (a) mordenite wherein the primary cation is Li, Na, HNa having at least 2% Na by weight, K, Ca, Sr, Ba, Ce, Zn or Cr;
(b) ferrierite wherein the primary metal cation is Li, Na, K, Ca, Sr, Ba, Ce or Fe;
(c) erionite ore;
(d) calcium erionite; and
(e) clinoptilolite ore, at a temperature of 250°-475° C. and a pressure of 7-7000 kPa, a contact time, normalized to 7 kPa, of 0.1 to 60 seconds, and a methanol conversion of 15-95%.

Ashina et al., Japanese published Patent Application No. 56-53887, and Mochida et al., *Journal of Catalysis* 82:313 (1981), also disclose use of mordenite zeolites to enhance production of dimethylamine in closely related variants of the process disclosed by Weigert.

Weigert, U.S. Pat. No. 4,313,003, discloses an improved process for disproportionating monomethylamine to dimethylamine and ammonia, comprising passing monomethylamine over a crystalline aluminosilicate catalyst selected from
(a) mordenite wherein the primary cation is Na, HNa having at least 2% Na, Mg, Ca, Sr or Ba;
(b) ferrierite wherein the primary metal cation is Na, K, Mg, Ca, Sr or Ba;
(c) clinoptilolite; and
(d) phillipsite,
at a temperature of 250°–475° C. and a pressure of 7–7000 kPa, at a feed rate of 0.1–10 grams of monomethylamine/per gram of catalyst per hour, at a monomethylamine conversion of 15–75%.

Cochran et al., U.S. Pat. No. 4,398,041, describe a process for converting $C_1$–$C_4$ alcohols to a non-equilibrium controlled distribution of primary, secondary, and tertiary alkylamines. The process disclosed involves passing a mixture of reactant alcohols and ammonia into a first conversion zone containing a "shape-selective" crystalline aluminosilicate catalyst having a pore size selective for mono- and disubstituted alkylamine products; dividing the resulting product stream; passing one portion of this product stream to a second conversion zone containing another catalyst having a different pore size distribution; and combining the remaining portion of the first product stream with the product stream of the second conversion zone to yield a non-equilibrium controlled product distribution. The zeolite catalysts disclosed by this reference include 5A zeolite, REY zeolite, H-chabazite-erionite, H-erionite, H-mordenite, and H-Y zeolite. Deeba et al., published European Patent Application No. 0085408, disclose a method for improving methanol conversion rates comprising reacting methanol and ammonia over a highly acidic dehydrated aluminosilicate catalyst having a silicon to aluminum ratio of at least 2.0 and manifesting microporous diffusivity for methylamines.

Deeba et al., U.S. Pat. No. 4,434,300, disclose a method for improving methanol conversion rates in the reaction of methanol and ammonia to produce methylamines which comprises effecting the reaction in the presence of a macroporous, highly acidic aluminosilicate.

Tompsett, U.S. Pat. No. 4,436,938, discloses a process for making methylamines comprising reacting methanol and/or dimethyl ether over a binderless zeolite A catalyst, preferably a binderless zeolite 5A catalyst. Toya Soda, Japanese Pat. No. 49,340, discloses use of hydrogen, alkaline earth metal, or rare earth metal form of a mordenite zeolite for the production of dimethylamine.

As the foregoing discussion suggests, new process improvements which optimize dimethylamine yields while suppressing production of trimethylamine in this widely-practiced process are desirable. Chabazite is a mineral found in many locations around the world. Although the x-ray diffraction patterns of chabazites from different locations are essentially identical, it has been found that different chabazites have markedly different catalytic activity. Since cabazites provide a relatively inexpensive catalyst, methods for selecting chabazites having improved catalytic activity are of significant interest to the chemical industry.

SUMMARY OF THE INVENTION

The present invention provides a process for producing dimethylamine comprising reacting methanol and/or dimethylether and ammonia in amounts sufficient to provide a carbon/nitrogen (C/N) ratio from about 0.2 to about 1.5, at a temperature from about 250° C. to about 450° C., in the presence of a catalytic amount of an acidic zeolite catalyst selected from the group consisting of natural, H-exchanged, and M-exchanged chabazites, each having a geometric selectivity index (GSI) greater than about 3, wherein M is one or more alkali metal ions selected from the group consisting of Na, K, Rb and Cs. The acidic zeolite catalyst provides, at a conversion of methanol and/or DME to methylamines in excess of about 85 percent on a mole basis, a selectivity to dimethylamine greater than about 40 percent on a mole basis.

The present invention further provides a method for selecting acidic zeolite catalyst selected from the group consisting of natural, H-exchanged, and M-exchanged chabazites having improved catalytic activity comprising determining a GSI for said acidic zeolite catalyst and selecting acidic zeolite catalyst having a GSI greater than about 3.

DETAILED DESCRIPTION OF THE INVENTION

Zeolites can be generically described as complex aluminosilicates characterized by a three-dimensional framework structure enclosing cavities occupied by ions and water molecules, all of which can move with significant freedom within the zeolite matrix. In commercially useful zeolites, the water molecules can be removed from or replaced within the framework without destroying its geometry. Zeolites can be represented by the following formula:

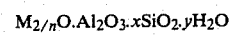

$$M_{2/n}O.Al_2O_3.xSiO_2.yH_2O$$

wherein M is a cation of valence n, $x \geq 2$, and y is a number determined by the porosity and the hydration state of the zeolite, generally from 2 to 8. In naturally-occurring zeolites, M is principally represented by Na, Ca, K, Mg and Ba in proportions usually reflecting their approximate geochemical abundance. The cations M are loosely bound to the structure and can frequently be completely or partially replaced with other cations by conventional ion exchange.

Zeolite structure consists of corner-linked tetrahedra with Al or Si atoms at centers of tetrahedra and oxygen atoms at corners. Such tetrahedra are combined in a well-defined repeating structure comprising various combinations of 4-, 6-, 8-, 10-, and 12-membered rings. The resulting framework consists of regular channels and cages, which impart a useful pore structure for catalysis. Pore dimensions are determined by the geometry of the aluminosilicate tetrahedra forming the zeolite channels or cages, with nominal openings of 2.6 angstroms for 6-rings, 4.0 angstroms for 8-rings, and 5.5 angstroms for 10-rings. Pore dimensions are critical to catalytic performance, since this zeolite characteristic determines whether reactant molecules can enter and product molecules can exit the zeolite framework. In practice, it has been observed that very slight decreses in ring dimensions can effectively hinder or block movement of particular reactants or products within a zeolite structure.

The pore dimensions which control access to the interior of the zeolite are determined not only by the tetrahedra forming the pore opening, but also by the presence or absence of ions in or near the pore. In the case of zeolite A, for example, access can be restricted by monovalent ions, such as Na+ or K+, which are situated in or near 8-ring openings as well as 6-ring openings. Access is enhanced by divalent ions, such as Ca$^{2+}$, which are situated only in or near 6-rings. Thus KA and NaA exhibit effective pore openings of about 0.3 nm and 0.4 nm respectively, whereas CaA has an effective pore opening of 0.5 nm.

Useful references generally relating to zeolite structure and characterization include the following:
Meier et al., Atlas of Zeolite Structure Types (International Zeolite Assn. 1978);
Mumpton, "Natural Zeolites" in Reviews in Mineralogy 14: 1 (1977);
Smith, "Origin and Structure of Zeolites" in Zeolite Chemistry and Catalysis, ACS Monograph 171 (American Chemical Society, 1976).

Characteristics of Chabazites

Chabazites have structures which comprise channels formed by repeating 8-rings. The structure of chabazite consists of identical, near-spherical "chabazite cages", each composed of two 6-rings at top and bottom, six 8-rings in rhombohedral positions, and six pairs of adjacent 4-rings. Each cage or pore is thus interconnected to six adjacent pores by near-planar, chair-shaped 8-rings. Chabazites can be characterized by the following formula:

$$M_a{}^n Al_{12}Si_{24}O_{72}.40H_2O.$$

In this formula, the product of a and n is 12. M generally includes Ca, Mg, Na and K.

The cationic species $M^{n+}$ present in chabazites can be exchanged for protons in a conventional ion exchange with H+ or by conversion to an ammoniated form (NH$_4$+-chabazite) which is subsequently converted to the H+ form by calcination at elevated temperatures.

Acid forms of zeolites can be prepared by a variety of techniques including ammonium exchange followed by calcination, direct exchange of alkali ions for protons using mineral acids or ion exchangers, and introduction of polyvalent ions (for a discussion of acid sites in zeolites, see Dwyer, "Zeolite Structure, Composition and Catalysis" in *Chemistry and Industry*, Apr. 2, 1984). The acid sites produced are generally believed to be of the Bronsted (proton donating) type or of the Lewis (electron pair accepting) type. Bronsted sites are generally produced by deammoniation at low temperatures, exchange with protons, or hydrolysis of polyvalent cations. Lewis sites are believed to arise from dehydroxylation of the H-zeolites or from the presence of polyvalent ions. In the acidic zeolite catalysts of the present invention, Bronsted and/or Lewis sites can be present.

Introduction of other alkali metal or alkaline earth metal cations into the structure of chabazites can alter the effective size of channels and thus facilitate or hinder passage of reactant or product molecules during a reaction. Thus, cation exchange can be employed as a means for enhancing selectivity of chabazites for dimethylamine.

Although pore dimensions of a given zeolite can be determined from X-ray studies of its crystal structure, this information is relatively expensive and laborious to obtain and does not necessarily indicate catalytic selectivity. However, pore accessibility can be determined simply and directly by obtaining sorption data, using a probe molecule of appropriate size. Sorption measurements are capable of detecting pore blockage and particular molecular constraints which are not necessarily detected by X-ray studies of crystal structure.

Accordingly, a criterion based upon empirical observations of zeolite sorption characteristics has been devised in order to assess the utility of various small-pore zeolites as catalysts for conversion of methanol and ammonia to dimethylamine. This criterion, which is herein designated the geometric selectivity index for dimethylamine, or GSI, is defined as net sorption of methanol (MeOH) divided by net sorption of n-propanol (n-PrOH), each measured at 25° C. following 20 hours' exposure to sorbate vapor. Sorption is expressed in weight percent, i.e., grams sorbate per 100 grams zeolite.

Sorption measurements are made using an apparatus substantially analogous to that described by Landolt, *Anal. Chem.* 43: 613 (1971). In a typical experiment, 0.4 to 1 g of zeolite is pressed at 300–1000 psi into a self-supporting cylinder, inserted into a preweighed sample holder, evacuated, heated to 425° C., cooled, and then weighed in the sample holder. A sample is then exposed to sorbate vapor at 10–50% of its vapor pressure at 25° C. in a sorption manifold, removed from the sorption manifold, and weighed again to determine sorption.

Zeolites exhibiting little appreciable methanol sorption, for example, less than 3 g methanol per 100 g zeolite, generally possess little catalytic activity for producing methylamines from methanol and ammmonia. Such zeolites include those with blocked channels or zeolites composed of 6-ring systems as the sole path of molecular transport within the framework. Zeolites with appreciable isopropanol sorption, for example, more than 3 g per 100 g zeolite, generally are associated with high ratios of TMA to DMA production. Active zeolites with sorptions of methanol or ethanol of about 10–25 g per 100 g zeolite and little or no isopropanol sorption produce monomethylamine and dimethylamine selectively versus trimethylamine.

It has been found that for chabazites, increases in GSI correlate with increases in selectivity for dimethylamine. Thus, the present invention provides a method for selecting acidic zeolite catalyst selected from the group consisting of natural, N-exchanged, and M-exchanged chabazites having improved catalytic activity. The method comprises determining a GSI for the acidic zeolite catalyst and selecting acidic zeolite catalyst having a GSI greater than about 3. Preferably, acidic zeolite catalyst selected by the present method are employed in the present process for producing dimethylamine.

The catalysts of the present invention are natural, H-exchanged, and M-exchanged chabazites exhibiting a GSI greater than about 3. Preferred catalysts are those chabazites, both natural and H-exchanged, having a GSI greater than about 4. The most preferred zeolite species for use in the process of the present invention are H-exchanged chabazites having a GSI greater than about 5.

Table I, below, lists sources and sorption data for several varieties of naturally-occurring mineral chabazites:

TABLE I

| Source | Mineral Chabazites Sorption (g/100 g) | | |
|---|---|---|---|
| | MeOH | n-PrOH | GSI |
| Naples, Italy | 13.5 | 2.6 | 5.2 |
| Nova Scotia, Canada | 20.9 | 4.8 | 4.4 |
| Durkee, Oregon | 17.2 | 4.8 | 3.6 |
| Beaver Divide, Wyoming | 11.5 | 4.1 | 2.8 |
| Christmas, Arizona | 17.7 | 6.6 | 2.7 |
| Wikieup, Arizona | 13.6 | 10.0 | 1.4 |
| Bear Springs, Arizona | 11.8 | 8.9 | 1.3 |
| Bowie, Arizona | 14.9 | 11.6 | 1.3 |

Catalyst Preparation

H-exchanged forms of natural, or mineral, chabazites, referred to herein simply as "H-chabazites", can be prepared by ion exchange with $NH_4^+$-ion containing solutions followed by calcination. Generally, calcination temperatures of from 400° C. to about 600° C. are satisfactory.

Cation-exchanged forms of chabazites, referred to herein as "M-chabazites", can be prepared from naturally-occurring chabazite forms or from H-chabazites by contacting a crystalline form of the zeolite with a solution containing the ion to be exchanged. Repeated applications of fresh solutions are necessary to obtain significant cation exchange. As used throughout the specification, the term "M-chabazite" refers to a cation-exchanged form wherein the cations M are selected from the group consisting of the alkali metal ions Na, K, Rb and Cs. Throughout the specification, particular forms of M-chabazites are referred to by a designation identifying the principal exchanged cation, for example, Na-chabazite or K-chabazite.

Process Conditions

As previously noted, the process of the present invention comprises reacting methanol and/or dimethylether (DME) and ammonia, in amounts sufficient to provide a carbon/nitrogen (C/N) ratio from about 0.2 to about 1.5, in the presence of natural, H-exchanged, or M-exchanged chabazites at a temperature from about 250° C. to about 450° C. Reaction pressures can be varied from 1-1000 psi (7-7000 kPa) with a methanol/DME space time of 0.01 to 80 hours. The resulting conversion of methanol and/or DME to methylamines is generally in excess of 85% (on a mole basis) and selectivity (on a mole basis) to dimethylamine is generally greater than 40%. In addition, selectivity to and yield of trimethylamine is suppressed. Thus, molar yields of dimethylamine generally exceed 40% and molar yields of trimethylamine generally are less than 30% under the process conditions of the present invention.

The process variables to be monitored in practicing the process of the present invention include C/N ratio, temperature, pressure, and methanol/DME space time. The latter variable is calculated as the mass of catalyst divided by the mass flow rate of methanol/DME introduced to a process reactor (mass catalyst/mass methanol+DME fed per hour).

Generally, if process temperatures are too low, low conversion of reactants to dimethylamine will result. On the other hand, if temperatures are excessively high, equilibrium conversions and catalyst deactivation can occur. Preferably, reaction temperatures are maintained between about 300° C. and 400° C. At relatively low pressures, products must be refrigerated to condense them for further purification, adding cost to the overall process. However, excessively high pressures require costly thick-walled reaction vessels. Preferably, pressures are maintained at 10-500 psi (70-3000 kPa). Short methanol/DME space times result in low conversions and tend to favor production of monomethylamine. Long methanol/DME space times may result either in inefficient use of catalyst or production of an equilibrium distribution of methylamines at very high conversions. Generally, methanol/DME space times of 0.01-80 hours are satisfactory, with methanol/DME space times of 0.10-1.5 hours being preferred (corresponding to methanol/DME space velocities of 0.013-100 g of methanol+DME/g of catalyst/hour, preferably 0.67-10 g of methanol+DME/g of catalyst/hour).

The molar reactant ratio of methanol and/or dimethylether to ammonia, herein expressed as the C/N ratio (g atoms C/g atoms N), is critical to the process of the present invention. As the C/N ratio is decreased, production of monomethylamine is increased. As the C/N ratio is increased, production of trimethylamine increases. Catalyst deactivation is also greater at high C/N ratios. Accordingly, for best results, C/N ratios should be maintained between 0.2 to 1.5, and preferably from 0.5 to 1.2 in conducting the process of the present invention.

The efficiency of the process of the invention is measured by overall conversion of methanol and/or DME to methylamines, and by selectivity of dimethylamine production. For example, if methanol is used as the sole reactant, overall conversion is determined by comparison of the amount (in moles) of methanol in the product mixture, which is considered to be unconverted, to the amount in the reactant feed. Thus, overall conversion, in percent, is given by:

$$100 \left[ 1 - \frac{\text{Moles MeOH in product}}{\text{Moles MeOH in feed}} \right]$$

Conversion of methanol to methylamines, in percent, is given by:

$$100 \left[ 1 - \frac{\text{Moles MeOH in product} + 2(\text{Moles } DME \text{ in Product})}{\text{Moles MeOH in Feed}} \right]$$

Conversion of methanol to monomethylamine (MMA), in percent, is given by:

$$100 \left[ \frac{\text{Moles } MMA}{\text{Moles MeOH in feed}} \right]$$

Similarly, conversion of methanol to dimethylamine (DMA), in percent, is given by:

$$100 \left[ \frac{2(\text{Moles } DMA)}{\text{Moles MeOH in feed}} \right]$$

and conversion of methanol to trimethylamine (TMA), in percent, is given by:

$$100\left[\frac{3(\text{Moles } TMA)}{\text{Moles MeOH in feed}}\right]$$

Finally, selectivity to DMA is calculated by analysis of product composition. Thus, selectivity to DMA, in percent, is provided by the following expression:

$$100\left[\frac{2[DMA]}{[MMA] + 2[DMA] + 3[TMA]}\right]$$

For efficient operation, the catalyst must be selective at high conversions (87–98%) and a C/N ratio of 0.5–1.2.

In practicing the process of the invention, the zeolite catalyst can be combined with another material resistant to the temperature and other conditions employed in the process. Such matrix materials include synthetic or natural substances such as clays, silica, and metal oxides.

Comparison of selectivities for different samples is best made at similar conversions since selectivity changes with conversion. At low conversions, MMA production is favored; at very high conversions, the reaction will approach an equilibrium distribution and thus result in increased TMA production.

The process of the present invention can be further understood by reference to the following Examples, wherein all temperatures are expressed in degrees Celsius (°C.) and all percentages are by weight unless otherwise indicated. In composition determinations, it was assumed that there were 72 oxygen atoms per unit cell. Analysis determined the relative amounts of the various cations present, and remaining positively-charged species were assumed to be hydrogen.

EXAMPLE 1

This example, and Examples 2–4, below, demonstrate the use of certain natural and H-exchanged chabazite minerals as catalysts in the process of the present invention.

Two grams of a catalyst consisting of 20–40 mesh particles of chabazite from Durkee, Oreg., were placed in a stainless-steel U-tube reactor 0.125 in (0.32 cm) in diameter and about 12 in (30 cm) in length. First, the reactor was heated to reaction temperature in a fluidized sand bath. The reaction pressure was maintained at atmospheric pressure, 14.7 lbs.-in$^{-2}$ (101 kPa). Reactants methanol and ammonia were fed to a preheater as a liquid mixture at a molar ratio of about 1, vaporized, and then passed through the reactor into contact with the catalyst sample. The reaction temperature and flow rate of reactants methanol and ammonia are set forth in Table II, below. The reactor effluent was continuously analyzed by gas chromatography for ammonia, dimethylether (DME), methanol, water, and mono-, di-, and trimethylamine. The percentage conversions of methanol (overall), of methanol to methylamines (MA), and the percentage selectivities of conversion to each methylamine species are given in Table II. That portion of methanol converted to other than methylamines was converted to DME in this and all other Examples reported herein.

EXAMPLE 2

In this example, an H-exchanged form of the chabazite employed in Example 1 was tested for catalytic activity. This material was prepared as follows. A 50 g sample of chabazite from Durkee, Oregon was heated at 500° for 10 hours. After calcination, the resulting material was contacted three times, for one hour each time, with 500 mL of a 10% NH$_4$NO$_3$ solution at 80°. The resulting sample was then dried and heated by raising the temperature 50° per hour to 500° where it was held for 10 hours. The resulting H-chabazite exhibited the following composition upon analysis: 0.63% MgO, 0.26% Na$_2$O, 0.38% CaO, 0.05% K$_2$O, 2.47% Fe$_2$O$_3$, 11.35% Al$_2$O$_3$, and 60.7% SiO$_2$; (Si/Al=4.53).

The sample was divided into 7 g portions. One portion was not treated further and H-chabazite from this portion was used in Example 2. Other portions were treted as described in Examples 7–9.

The resulting catalyst material was evaluated in an experiment conducted substantially similarly to that reported in Example 1, above. The conditions and results are set forth in Table II, below.

EXAMPLE 3

30 g of a mineral chabazite from Tufocampano, Italy (Naples) were heated in flowing air at 500° for 10 hours. The resulting sample was then contacted three times, for one hour each time, with a 10% NH$_4$NO$_3$ solution at 80°. The resulting ammoniated material was then dried and heated in flowing N$_2$ in stepwise fashion, increasing the temperature 50° per hour to 500°, followed by 10 hours at 500°. The resulting H-chabazite exhibited the following composition upon analysis: 0.395 Na$_2$O, 1.34% K$_2$O, 0.55% MgO, 0.78% CaO, 3.33% FeO, 13.05% Al$_2$O$_3$, and 62.25% SiO$_2$; (Si/Al=4.05). Hexagonal unit cell dimensions derived from an X-ray diffraction pattern were a=1.376 nm and c=1.472 nm.

This material was evaluated substantially according to the procedure of Example 1, above. The conditions employed and the results obtained are set forth in Table II, below.

EXAMPLE 4

50 g of a mineral chabazite from Christmas, Arizona, were heated in flowing N$_2$ at 500° for 10 hours. The resulting sample was then contacted three times, for one hour each time, with a 10% NH$_4$NO$_3$ solution at 80°. The resulting ammoniated material was then dried and heated in flowing N$_2$ in stepwise fashion, increasing temperature 50° per hour to 500°, followed by 10 hours at 500°. The resulting H-chabazite exhibited the following composition upon analysis: 0.17% Na$_2$O, 0.11% K$_2$O, 0.56% MgO, 0.17% CaO, 2.2% FeO, 12.58% Al$_2$O$_3$, and 63.40% SiO$_2$; (Si/Al=4.23). Hexagonal unit cell dimensions derived from an X-ray diffraction pattern were a=1.373 nm and c=1.474 nm.

This material was evaluated substantially according to the procedure of Example 1, above. The conditions employed and the results obtained are set forth in Table II, below:

TABLE II

Catalytic Performance of Selected Natural and H—Exchanged Chabazites

| Example | Catalyst (Source) | T (°C.) | Feed Flow (mL/hr) | MeOH Conv. (%) | MeOH—MA Conv. (%) | Selectivity (%) MMA | DMA | TMA |
|---|---|---|---|---|---|---|---|---|
| 1 | chabazite (Durkee) | 400 | 1 | 97 | 92 | 21 | 45 | 34 |
| 2 | H—chabazite (Durkee) | 400 | 4 | 98 | 93 | 16 | 51 | 33 |
| 3 | H—chabazite (Naples) | 350 | 2 | 98 | 98 | 23 | 59 | 18 |
| 4 | H—chabazite (Christmas) | 400 | 8 | 98 | 93 | 16 | 41 | 43 |

EXAMPLES 5, 6-COMPARATIVE EXPERIMENTS A, B

Examples 5 and 6 and Comparative Experiments A and B illustrate use of GSI determinations to predict catalytic performance of selected chabazite minerals. As noted previously, increased GSI correlates with increased dimethylamine selectivity for chabazite zeolites.

Sorption measurements employed in determining GSI were carried out according to the following procedure, which is described for the material employed as catalyst in Example 5. A sample of 1.0980 g of Ca, K-chabazite from a location near Naples, Italy, was placed in a preweighed cell and evacuated. The sample was slowly heated to 425° under vacuum and held at 425° for 18 hours. After exposing the sample to 375 mm $O_2$ for 30 minutes to oxidize any organic material present, the sample was evacuated at 425° until the pressure reached $3.7 \times 10^{-5}$ mm Hg. The sample weight then equaled 0.9063 g. The sample was then exposed to 38 mm Hg methanol vapor for 20 hours. Another weighing of the methanol-exposed sample indicated that 0.1257 g methanol had been sorbed, corresponding to 13.84 g methanol per 100 g zeolite. Substraction of 0.37 g methanol per 100 g zeolite, to account for absorption to the external surface of the zeolite, indicated a net sorption of 13.47 g methanol per 100 g zeolite. The net quantities of n-propanol sorbed were determined using a substantially similar procedure. Other chabazites employed in Example 6 and Comparative Experiments A and B were tested in like manner. The results were used to calculate GSI as previously described. The resulting GSI determinations and the results of catalyst evaluation experiments conducted substantially as described in Example 1 are set forth in Table III, below.

sults are obtained when an alumina-silica catalyst (91% $Al_2O_3$, 6.5% $SiO_2$) is employed.

COMPARATIVE EXPERIMENT C

Zeolite H-ferrierite was prepared by heating a sample of ferrierite (Zeolon ® 700, Norton Company) to 500° in flowing $N_2$ for 10 hours and then contacting the resulting saple three times, for one hour each time, with a 10% $NH_4NO_3$ solution at 80°. The resulting material was dried and heated by increasing the temperature 50° per hour to 500°, and then held at 500° for ten hours. The resulting sample of H-ferrierite was then cooled and evaluated for dimethylamine selectivity by a procedure substantially similar to that described in Example 1. The conditions employed and the results obtained are set forth in Table IV, below.

COMPARATIVE EXPERIMENT D

Zeolite H-erionite was prepared from a sample of zeolite $NH_4$-erionite (Linde E-10) by a procedure substantially similar to that described for preparation of H-ferrierite in Comparative Experiment C. The resulting material was evaluated for dimethylamine selectivity substantially according to the procedure of Example 1. The results obtained are set forth in Table IV, below.

COMPARATIVE EXPERIMENT E

Methanol and ammonia were passed over a catalyst consisting of 2 g of zeolite H-silicalite (S-115, Union Carbide Corporation) substantially as described in Example 1. The conditions and results are displayed in Table IV. This material sorbed 12.5 g methanol and 12.5 g n-propanol per 100 g catalyst, providing a GSI of 1.

COMPARATIVE EXPERIMENT F 100 g of zeolite $NH_4$-Y (Linde LZY-82) were cal-

TABLE III

Comparison of GSI and Catalytic Performance of Selected Natural Chabazite Zeolites

| Example | Zeolite (Source) | GSI | T (°C.) | Feed Flow (mL/hr) | MeOH Conv. (%) | Selectivity MMA | DMA | TMA |
|---|---|---|---|---|---|---|---|---|
| 5 | Ca,K—chabazite (Naples) | 5.2 | 400 | 2 | 96 | 20 | 55 | 24 |
| 6 | Ca,K—chabazite (Durkee) | 3.6 | 400 | 1 | 97 | 21 | 45 | 34 |
| Comparative Experiment | | | | | | | | |
| A | Ca,K—chabazite (Christmas) | 2.7 | 400 | 2 | 98 | 16 | 33 | 51 |
| B | Na—chabazite (Bowie) | 1.3 | 400 | 4 | 95 | 13 | 23 | 64 |

COMPARATIVE EXPERIMENTS C-G

Comparative Experiments C-G demonstrate that some zeolites having ports bounded by 8 aluminosilicate tetrahedra, for example, erionite, and zeolites having ports bounded by 10 or 12 aluminosilicate tetrahedra, for example, ferrierite, silicalite, and zeolite Y, display little or no selectivity to dimethylamine when compared to the values attained at equilibrium for the uncatalyzed reaction of methanol and ammonia. Similar recined in air by heating in 50° stepwise increments to 540°, and then held at 540° for about 10 hours. The resulting product, zeolite H-Y, was evaluated for dimethylamine selectivity by a procedure substantially similar to that described in Example 1. The conditions and results are set forth in Table IV.

COMPARATIVE EXPERIMENT G

In a procedure substantially similar to that described in Example 1, methanol and ammonia were passed over a catalyst consisting of 2 g of silica-alumina (91% Al$_2$O$_3$, 6.5% SiO$_2$; Harshaw Chemical Co., Al-1602T). The conditions and results are displayed in Table IV, below.

TABLE IV

Methylamine Selectivities of Erionite, Selected 10- and 12-Ring Zeolites, and Silica-Alumina Catalysts

| Comparative Experiment | Catalyst | T (°C.) | Feed Flow (mL/hr) | MeOH Conv. (%) | MeOH—MA Conv. (%) | Selectivity (%) | | |
|---|---|---|---|---|---|---|---|---|
| | | | | | | MMA | DMA | TMA |
| C | H—ferrierite | 400 | 0.5 | 94 | 90 | 13 | 28 | 59 |
| D | H—erionite | 400 | 2 | 98 | 98 | 18 | 31 | 51 |
| E | H—silicalite | 400 | 4 | 97 | 92 | 9 | 22 | 69 |
| F | H—Y LZY-82 | 300 | 4 | 94 | 70 | 1 | 4 | 95 |
| G | Harshaw Al 1602 | 400 | 6 | 92 | 80 | 11 | 14 | 75 |
| | Equilibrium | 400 | | | | 10 | 22 | 68 |

EXAMPLES 7-9

Examples 7 through 9 illustrate preparation and use of selected M-chabazites, specifically Na-, K- and Cs- forms of mineral chabazite obtained from Durkee, Oregon.

Some of the portions of zeolite H-chabazite (Durkee) prepared as described in Example 2 were contacted with 70 mL of a solution containing a selected cation to be exchanged, for one hour at 80°, followed by filtration and washing with H$_2$O, and drying at 150°. Thus, Na-chabazite (Durkee) was prepared using NaNO$_3$ as the exchange solution, K-chabazite was prepared using KNO$_3$, and Cs-chabazite was prepared using CsOH. These materials were evaluated as Examples 7, 8, and 9, respectively, using a procedure substantially similar to that described in Example 1, above. The conditions and results are shown in Table V, below.

TABLE V

Comparison of Catalytic Selectivity of Selected Cation-Exchanged Chabazite Minerals

| Example | Zeolite | T. (°C.) | Feed Flow (mL/hr) | MeOH Conv. (%) | MeOH—MA Conv. (%) | Selectivity (%) | | |
|---|---|---|---|---|---|---|---|---|
| | | | | | | MMA | DMA | TMA |
| 7 | Na—chabazite (Durkee) | 400 | 12 | 97 | 96 | 20 | 61 | 19 |
| 8 | K—chabazite (Durkee) | 400 | 12 | 98 | 97 | 19 | 63 | 18 |
| 9 | Cs—chabazite (Durkee) | 400 | 11 | 97 | 91 | 26 | 60 | 14 |

What is claimed is:

1. A process for producing dimethylamine consisting essentially of the step of reacting methanol and/or dimethylether (DME) and ammonia, in amounts sufficient to provide a carbon/nitrogen (C/N) ratio from about 0.2 to about 1.5, at a temperature from about 250° C. to about 450° C., in the presence of a catalytic amount of acidic zeolite catalyst selected from the group consisting of natural, H-exchanged, and M-exchanged chabazites, each having a geometric selectivity index greater than about 3, wherein M is one or more alkali metal ions selected from the group consisting of Na, K, Rb, and Cs; said reaction providing a conversion of methanol and/or DME to methylamines in excess of about 85 percent on a mole basis and a selectivity to dimethylamine greater than about 40 percent on a mole basis.

2. A process according to claim 1, conducted at a pressure from 7 to 7000 kPa and at a reactant feed rate sufficient to provide a methanol/DME space time of 0.01 to 80 hours.

3. A process according to claim 2, wherein the temperature is from 300° C. to 400° C.

4. A process according to claim 3, wherein the pressure is from 70 to 3000 kPa, and the methanol/DME space time is from 0.20 to 1.5 hours.

5. A process according to claim 4, wherein the C/N ratio is from about 0.5 to about 1.2.

6. A process according to claim 5, wherein the catalyst is a natural chabazite having a geometric selectivity index greater than about 4.

7. A process according to claim 6, wherein the catalyst is a natural chabazite having a geometric selectivity index greater than about 5.

8. A process according to claim 5, wherein the catalyst is an H-chabazite.

9. A process according to claim 8, wherein the catalyst is an H-chabazite having a geometric selectivity index greater than about 4.

10. A process according to claim 9, wherein the catalyst is an H-chabazite having a geometric selectivity index greater than about 5.

11. A process according to claim 5, wherein the catalyst is an M-chabazite.

12. A process according to claim 11, wherein M is Rb.

13. A process according to claim 11, wherein M is Na.

14. A process according to claim 11, wherein M is K.

15. A process according to claim 11, wherein M is Cs.

* * * * *